United States Patent
He et al.

(10) Patent No.: US 12,263,016 B2
(45) Date of Patent: Apr. 1, 2025

(54) HOSPITAL BED AND MAGNETIC RESONANCE IMAGING SYSTEM

(71) Applicant: Siemens Healthcare GmbH, Erlangen (DE)

(72) Inventors: Chao Ming He, Shenzhen (CN); Ting Qiang Xue, Shenzhen (CN); Bin Kuang, Shenzhen (CN)

(73) Assignee: Siemens Healthineers AG, Erlangen (DE)

( * ) Notice: Subject to any disclaimer, the term of this patent is extended or adjusted under 35 U.S.C. 154(b) by 393 days.

(21) Appl. No.: 17/939,123

(22) Filed: Sep. 7, 2022

(65) Prior Publication Data

US 2023/0075663 A1    Mar. 9, 2023

(30) Foreign Application Priority Data

Sep. 7, 2021   (CN) .......................... 202111052861.0

(51) Int. Cl.
    *A61B 5/00*    (2006.01)
    *A61B 5/055*    (2006.01)
(52) U.S. Cl.
    CPC .............. *A61B 5/704* (2013.01); *A61B 5/055* (2013.01)

(58) Field of Classification Search
    CPC .. A61B 5/00; A61B 5/70; A61B 5/704; A61B 5/055
    See application file for complete search history.

(56) References Cited

U.S. PATENT DOCUMENTS

| | | | |
|---|---|---|---|
| 5,590,429 A * | 1/1997 | Boomgaarden | A61G 13/04 5/601 |
| 7,654,382 B2 | 2/2010 | Farooqui | |
| 7,874,031 B2 * | 1/2011 | Großhauser et al. | A61B 5/055 5/601 |

* cited by examiner

*Primary Examiner* — Fredrick C Conley
(74) *Attorney, Agent, or Firm* — Banner & Witcoff Ltd.

(57) ABSTRACT

A hospital bed may include a bed frame, a first bed board and an auxiliary component. The first bed board is connected to the bed frame. The auxiliary component may include a connecting frame, a first moving and supporting mechanism and a second bed board. The connecting frame is detachably connected to the first bed board. The first moving and supporting mechanism is connected to the connecting frame. The second bed board is connected to the first moving and supporting mechanism and can carry an object along the bearing direction. The second bed board is arranged on one side of the first bed board along the bearing direction. The first moving and supporting mechanism can drive the second bed board to move relative to the first bed board along an adjustment direction, where the adjustment direction is perpendicular to the bearing direction.

11 Claims, 7 Drawing Sheets

HOSPITAL BED AND MAGNETIC RESONANCE IMAGING SYSTEM

CROSS REFERENCE TO RELATED APPLICATIONS

This patent application claims priority to Chinese Patent Application No. 202111052861.0, filed Sep. 7, 2021, which is incorporated herein by reference in its entirety.

BACKGROUND

Field

The present disclosure relates to a hospital bed, and in particular to a hospital bed that can be used in a magnetic resonance imaging system.

Related Art

Magnetic resonance imaging (MRI) is a medical imaging technology that can be used for disease diagnosis. The hospital bed for a magnetic resonance imaging system is used to move an object to be scanned to the scanning region of the magnetic resonance imaging system. At present, most hospital beds are configured as such that the object to be scanned can only be moved along the axial direction of the access hole of the magnetic resonance imaging system and the height direction of the hospital bed. For large-aperture magnetic resonance imaging systems, the optimal scanning region is limited to the central part of the access hole. In order to achieve a better imaging result, it is necessary to move the to-be-scanned part of the object to be scanned to the optimal scanning region. However, existing hospital beds cannot be used for the lateral movement of an object to be scanned.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

Figure 1:
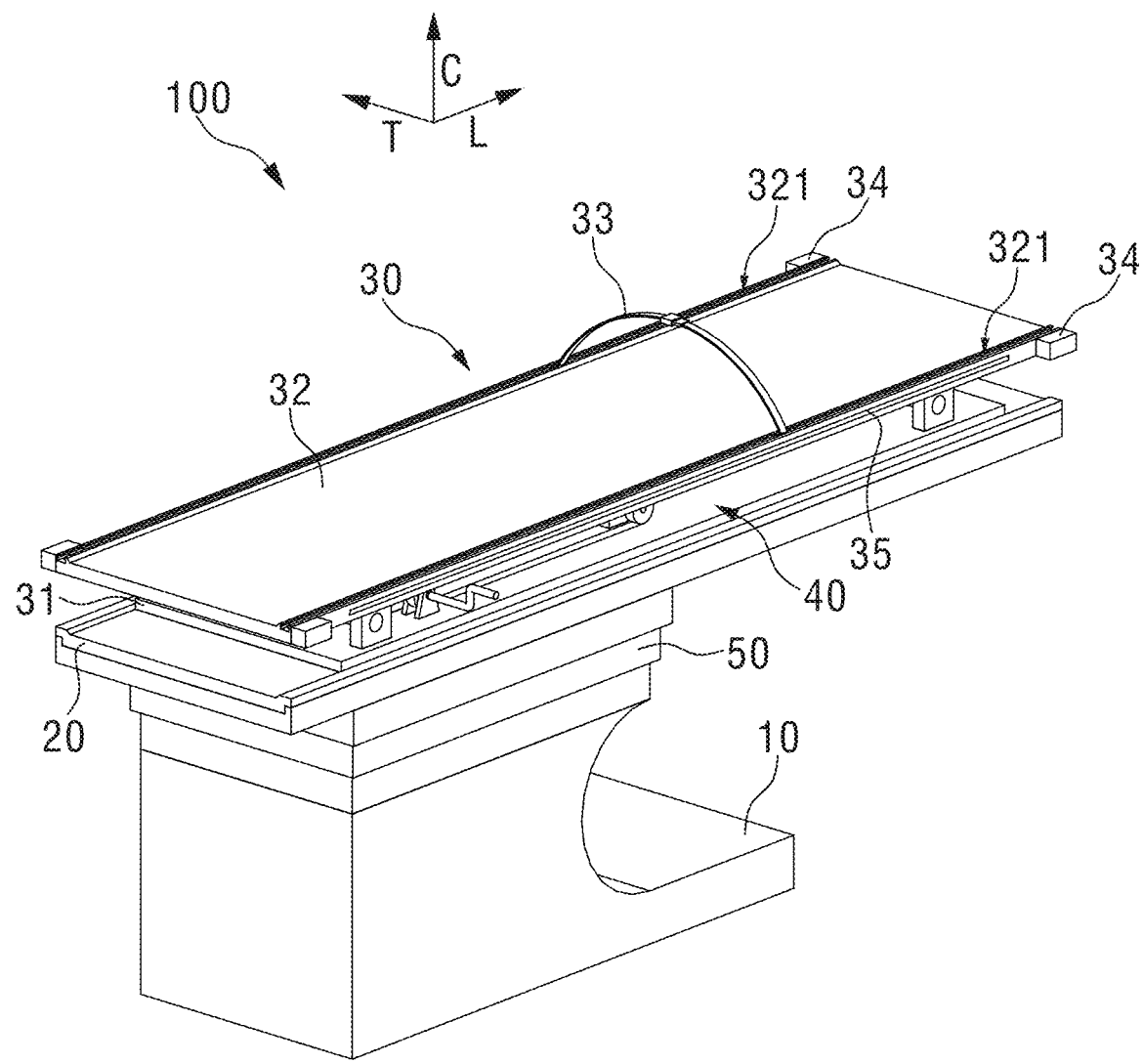
FIG. 1 is a patient bed according to an exemplary embodiment of the present disclosure.

The exemplary embodiments of the present disclosure will be described with reference to the accompanying drawings. Elements, features and components that are identical, functionally identical and have the same effect are—insofar as is not stated otherwise—respectively provided with the same reference character.

DETAILED DESCRIPTION

In the following description, numerous specific details are set forth in order to provide a thorough understanding of the embodiments of the present disclosure. However, it will be apparent to those skilled in the art that the embodiments, including structures, systems, and methods, may be practiced without these specific details. The description and representation herein are the common means used by those experienced or skilled in the art to most effectively convey the substance of their work to others skilled in the art. In other instances, well-known methods, procedures, components, and circuitry have not been described in detail to avoid unnecessarily obscuring embodiments of the disclosure. The connections shown in the figures between functional units or other elements can also be implemented as indirect connections, wherein a connection can be wireless or wired. Functional units can be implemented as hardware, software or a combination of hardware and software.

An object of the present disclosure is to provide a hospital bed that can laterally move an object to be scanned. Another object is to provide a magnetic resonance imaging system with a hospital bed capable of laterally moving an object to be scanned.

Exemplary embodiments of the present disclosure provide a hospital bed, which may comprise a bed frame, a first bed board and an auxiliary component. The first bed board may be connected to the bed frame and can carry an object along a bearing direction. The auxiliary component comprises a connecting frame, a first moving and supporting mechanism and a second bed board. The connecting frame may be detachably connected to the first bed board. The first moving and supporting mechanism may be connected to the connecting frame. The second bed board may be connected to the first moving and supporting mechanism and can carry an object along the bearing direction. The second bed board may be arranged on one side of the first bed board along the bearing direction. The first moving and supporting mechanism can act to drive the second bed board to move relative to the first bed board along an adjustment direction, wherein the adjustment direction may be perpendicular to the bearing direction.

The hospital bed can be used for lateral movement of an object to be scanned carried on the second bed board along an adjustment direction.

In another exemplary embodiment of the hospital bed, the first moving and supporting mechanism may comprise a screw, a moving block and a supporting assembly. The screw may be rotatably connected to the connecting frame. The axial direction of the screw may be parallel to the adjustment direction. The moving block may be fixedly connected to the second bed board and threadedly connected to the screw. The supporting assembly comprises a sliding rod and a set of sliders. The sliding rod may be fixedly connected to either the connecting frame or the second bed board and extends along the adjustment direction. The set of sliders may be fixedly connected to either the connecting frame or the second bed board, whichever not fixedly connected to the sliding rod, and may be slidably sleeved on the sliding rod. The structure is simple and has good stability.

In yet another exemplary embodiment of the hospital bed, the first moving and supporting mechanism may be provided with two supporting assemblies. The two supporting assemblies may be arranged along the length direction of the second bed board. The screw and the moving block may be arranged between the two supporting assemblies along the length direction of the second bed board, wherein the length direction of the second bed board may be perpendicular to the bearing direction and the adjustment direction. This helps to improve stability.

In still another exemplary embodiment of the hospital bed, the first moving and supporting mechanism further comprises a first transmission wheel, a second transmission wheel, a transmission belt and a drive member. The first transmission wheel may be fixedly connected to one end of the screw coaxially. The second transmission wheel may be rotatably connected to the connecting frame. The second transmission wheel and the first transmission wheel may be arranged along the length direction of the second bed board. The transmission belt may be wound on the first transmission wheel and the second transmission wheel. The drive member may be connected to the second transmission wheel to drive the second transmission wheel. The drive member may be configured as a handle or a drive motor. With the first transmission wheel, the second transmission wheel and the transmission belt, the position of the drive member can be flexibly set to drive the rotation of the screw.

In still another exemplary embodiment of the hospital bed, the auxiliary component further comprises a restraint belt. The second bed board has a runner on each of its two ends along the adjustment direction. The runner extends along the length direction of the second bed board, wherein the length direction of the second bed board may be perpendicular to the adjustment direction and the bearing direction. The two ends of the restraint belt may be respectively slidably set in the runners. This helps to prevent the object to be scanned from being squeezed by the second bed board and the wall of the access hole when the second bed board moves in the adjustment direction.

In still another exemplary embodiment of the hospital bed, the auxiliary component further comprises two laser intrusion detectors and a control mechanism. The detection regions of the two laser intrusion detectors may be respectively arranged on the two sides of the second bed board along the adjustment direction. The control mechanism may be capable of controlling the action of the first moving and supporting mechanism or sending an alarm based on an output signal of the laser intrusion detectors. This helps to prevent the object to be scanned from being squeezed by the second bed board and the wall of the access hole when the second bed board moves in the adjustment direction.

In still another exemplary embodiment of the hospital bed, the auxiliary component further comprises a plurality of pressure sensors and a control mechanism. The plurality of pressure sensors may be connected to the second bed board and arranged on the two sides of the second bed board along the adjustment direction. The control mechanism may be capable of controlling the action of the first moving and supporting mechanism or sending an alarm based on an output signal of the pressure sensors. This helps to prevent the object to be scanned from being squeezed by the second bed board and the wall of the access hole when the second bed board moves in the adjustment direction.

In yet another exemplary embodiment of the hospital bed, the connecting frame and the first moving and supporting mechanism may be arranged on the side of the second bed board facing the first bed board along the bearing direction. The first bed board has a plurality of mounting and positioning grooves provided along a direction opposite to the bearing direction. The connecting frame has a plurality of mounting and positioning portions. Each of the mounting and positioning portions may be inserted into one of the mounting and positioning grooves along a direction opposite to the bearing direction, to limit the relative displacement of the first bed board and the connecting frame along a direction perpendicular to the bearing direction. The auxiliary component further comprises a plurality of connecting bolts. Each of the connecting bolts penetrates one of the mounting and positioning portions in a direction opposite to the bearing direction, passes through the groove wall of one of the mounting and positioning grooves, and may be threadedly connected to the first bed board. The structure is simple and easy to assemble.

In still another exemplary embodiment of the hospital bed, the hospital bed further comprises a second moving and supporting mechanism. The second moving and supporting mechanism may be connected to the bed frame and the first bed board. The second moving and supporting mechanism can act to drive the first bed board to move along the length direction of the first bed board and the bearing direction, wherein the length direction of the first bed board, the bearing direction and the adjustment direction may be perpendicular to each other, and the length direction of the first bed board may be parallel to the length direction of the second bed board.

The present disclosure also provides a magnetic resonance imaging system, which comprises a magnetic field generating mechanism and a hospital bed described above. The magnetic field generating mechanism has an access hole extending in a linear direction. The magnetic field generating mechanism can generate a main magnetic field and a gradient magnetic field required for magnetic resonance imaging in the access hole. Both the length direction of the first bed board and the length direction of the second bed board may be parallel to the extension direction of the access hole. The adjustment direction may be perpendicular to the length direction of the first bed board and the bearing direction. The first bed board can extend into the access hole along the extension direction of the access hole. The hospital bed of the magnetic resonance imaging system can be used for lateral movement of an object to be scanned carried on the second bed board along the adjustment direction.

FIG. 1 is a schematic structural diagram of an exemplary embodiment of the hospital bed. As shown in FIG. 1, the hospital bed 100 comprises a bed frame 10, a first bed board 20 and an auxiliary component 30. The first bed board 20 may be connected to the bed frame 10 and can carry an object along a bearing direction C. In this exemplary embodiment, the hospital bed 100 further comprises a second moving and supporting mechanism 50. The second moving and supporting mechanism 50 may be connected to the bed frame 10 and the first bed board 20. The second moving and supporting mechanism 50 can act to drive the first bed board 20 to move along the length direction of the first bed board 20 and the bearing direction C.

As shown in FIG. 1, the auxiliary component 30 comprises a connecting frame 31, a first moving and supporting mechanism 40 and a second bed board 32. The connecting frame 31 may be detachably connected to the first bed board 20. The connecting frame 31 may be detachably connected to the first bed board 20 by, for example, bolts. After the connecting frame 31 may be removed from the first bed board 20, the auxiliary component 30 may be separated from the first bed board 20, and the first bed board 20 can carry an object along the bearing direction C. The first moving and supporting mechanism 40 may be connected to the connecting frame 31. The second bed board 32 may be connected to the first moving and supporting mechanism 40 and can carry an object along the bearing direction C. The second bed board 32 may be arranged on one side of the first bed board 20 along the bearing direction C, and the length direction of the first bed board 20 may be parallel to the length direction L of the second bed board 32. The first moving and supporting mechanism 40 can act to drive the second bed board 32 to move relative to the first bed board 20 along an adjustment direction T, wherein the adjustment direction T, the bearing direction C and the length direction L of the second bed board 32 may be perpendicular to each other.

Figure 2:
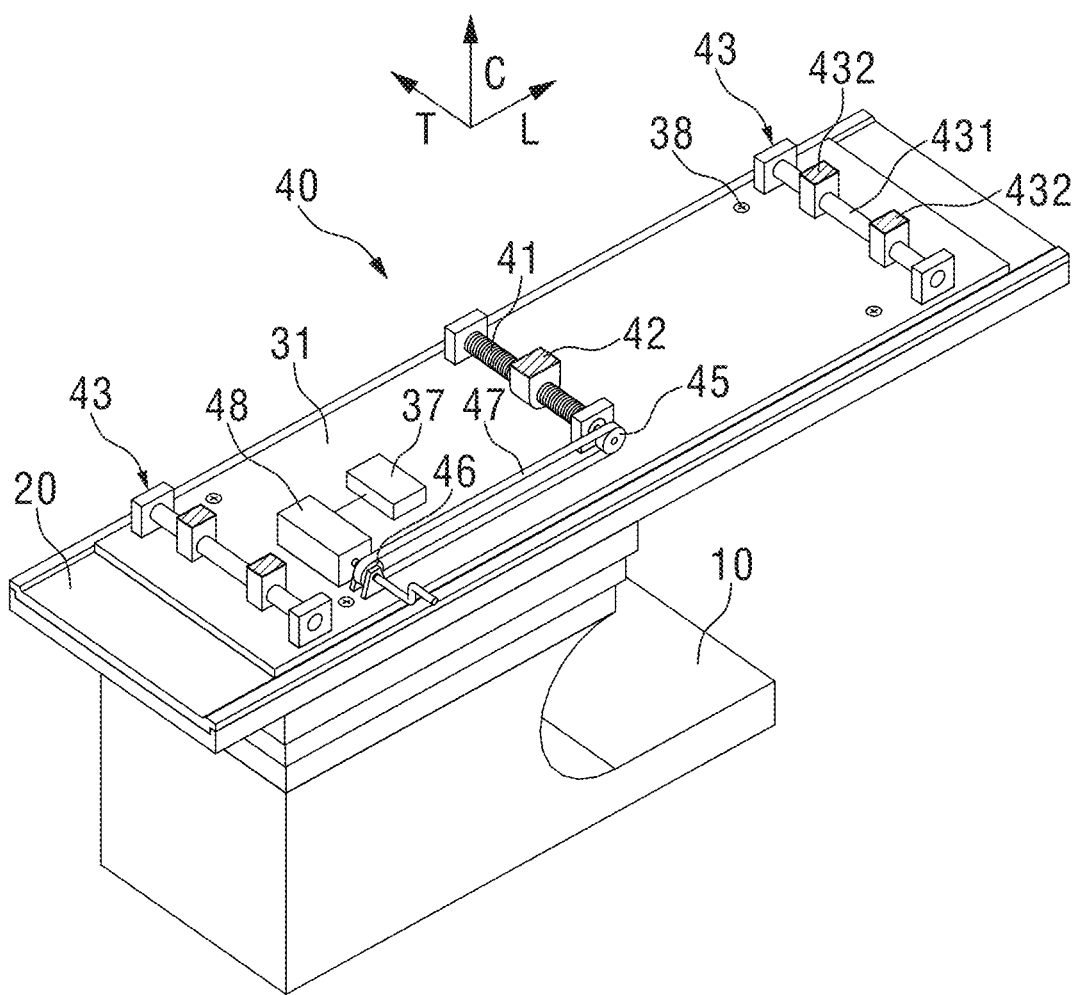
FIG. 2 is a section view of the bed showing the first moving and supporting mechanism according to an exemplary embodiment of the present disclosure.

FIG. 2 is a section view used to illustrate the first moving and supporting mechanism of the hospital bed in FIG. 1. As shown in FIG. 2, specifically, in this exemplary embodiment, the first moving and supporting mechanism 40 comprises a screw 41, a moving block 42 and a supporting assembly 43. The screw 41 may be rotatably connected to the connecting frame 31. The axial direction of the screw 41 may be parallel to the adjustment direction T. The moving block 42 may be fixedly connected to the second bed board 32 and threadedly connected to the screw 41. Each of the supporting assemblies 43 comprises a sliding rod 431 and a set of sliders 432. The sliding rod 431 may be fixedly connected to the connecting frame 31 and extends along the adjustment direction T. The set of sliders 432 may be fixedly connected to the second bed board 32 and may be slidably sleeved on the sliding rod 431. When in use, the screw 41 may be rotated to drive the second bed board 32 to move along the adjustment direction T. In this way, the hospital bed can be used for lateral movement of an object to be scanned carried on the second bed board along an adjustment direction.

In addition, in this exemplary embodiment, the second bed board can be moved in three directions perpendicular to each other (the bearing direction, the length direction of the second bed board and the adjustment direction) by means of the first and the second moving and supporting mechanisms, thereby an object to be scanned carried on the second bed board, when in the access hole of the magnetic resonance imaging system, can be scanned along the three directions perpendicular to each other so that the to-be-scanned position of the object to be scanned can be moved to the optimal scanning region.

In this exemplary embodiment, the first moving and supporting mechanism 40 may be provided with two supporting assemblies 43, but is not limited thereto. In other exemplary embodiments, the number of supporting assemblies 43 can be adjusted as needed.

As shown in FIG. 2, in the exemplary embodiment, the two supporting assemblies 43 may be arranged along the length direction L of the second bed board 32. The screw 41 and the moving block 42 may be arranged between the two supporting assemblies 43 along the length direction L of the second bed board 32. This helps to improve stability.

As shown in FIG. 2, in the exemplary embodiment, the first moving and supporting mechanism 40 further comprises a first transmission wheel 45, a second transmission wheel 46, a transmission belt 47 and a drive member 48. The first transmission wheel 45 may be fixedly connected to one end of the screw 41 coaxially. The second transmission wheel 46 may be rotatably connected to the connecting frame 31. The second transmission wheel 46 and the first transmission wheel 45 may be arranged along the length direction L of the second bed board 32. The transmission belt 47 may be wound on the first transmission wheel 45 and the second transmission wheel 46. The drive member 48 may be connected to the second transmission wheel 46 to drive the second transmission wheel 46. The two drive members 48 may be respectively configured as a handle and a drive motor, thereby the screw 41 can be driven to rotate both manually and by the motor. However, it is not limited thereto. In other exemplary embodiments, the first moving and supporting mechanism 40 may be provided with only one drive member 48, and the drive member 48 may be configured as a handle or a drive motor. With the first transmission wheel 45, the second transmission wheel 46 and the transmission belt 47, the position of the drive member 48 can be flexibly set to drive the rotation of the screw 41. For example, the drive member 48 configured as a drive motor may be arranged at one end of the second bed board 32 along its length direction L, so as to prevent the drive motor from entering the scanning region of the magnetic resonance imaging system.

As shown in FIG. 1, in the exemplary embodiment, the connecting frame 31 and the first moving and supporting mechanism 40 may be arranged on the side of the second bed board 32 facing the first bed board 20 along the bearing direction C, and concealing the first moving and supporting mechanism 40 between the first bed board 20 and the second bed board 32 helps to improve safety during use.

Figure 3:
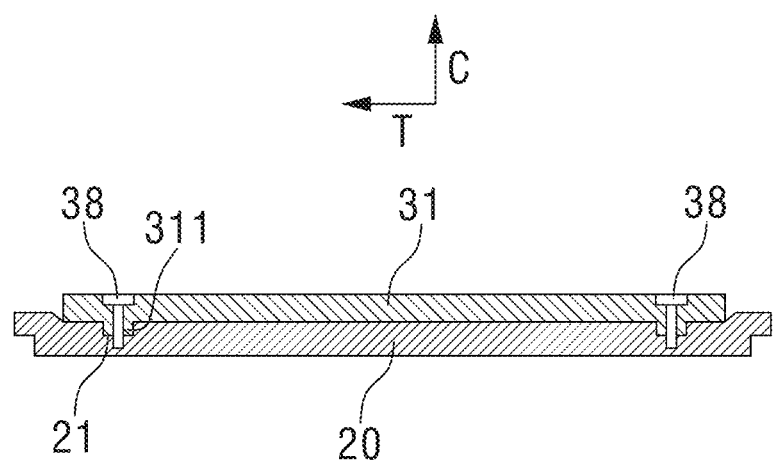
FIG. 3 is a section view of the bed showing the connection relationship between the first bed board and the connecting frame according to an exemplary embodiment of the present disclosure.

FIG. 3 is a section view used to illustrate the connection relationship between the first bed board and the connecting frame of the hospital bed in FIG. 1. As shown in FIG. 3, in the exemplary embodiment, the first bed board 20 has a plurality of mounting and positioning grooves 21 provided along a direction opposite to the bearing direction C. The connecting frame 31 has a plurality of mounting and positioning portions 311. Each of the mounting and positioning portions 311 may be inserted into one of the mounting and positioning grooves 21 along a direction opposite to the bearing direction C, to limit the relative displacement of the first bed board 20 and the connecting frame 31 along a direction perpendicular to the bearing direction C. The auxiliary component 30 further comprises a plurality of connecting bolts 38. Each of the connecting bolts 38 penetrates one of the mounting and positioning portions 311 in a direction opposite to the bearing direction C, passes through the groove wall of one of the mounting and positioning grooves 21, and may be threadedly connected to the first bed board 20. The structure is simple and easy to assemble.

Figure 4:
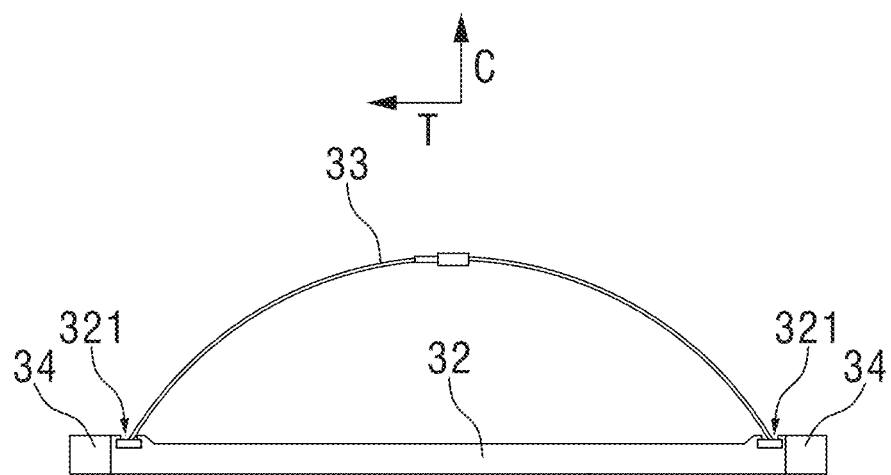
FIG. 4 is a side view of a partial structure of the bed according to an exemplary embodiment of the present disclosure.
Figure 5:
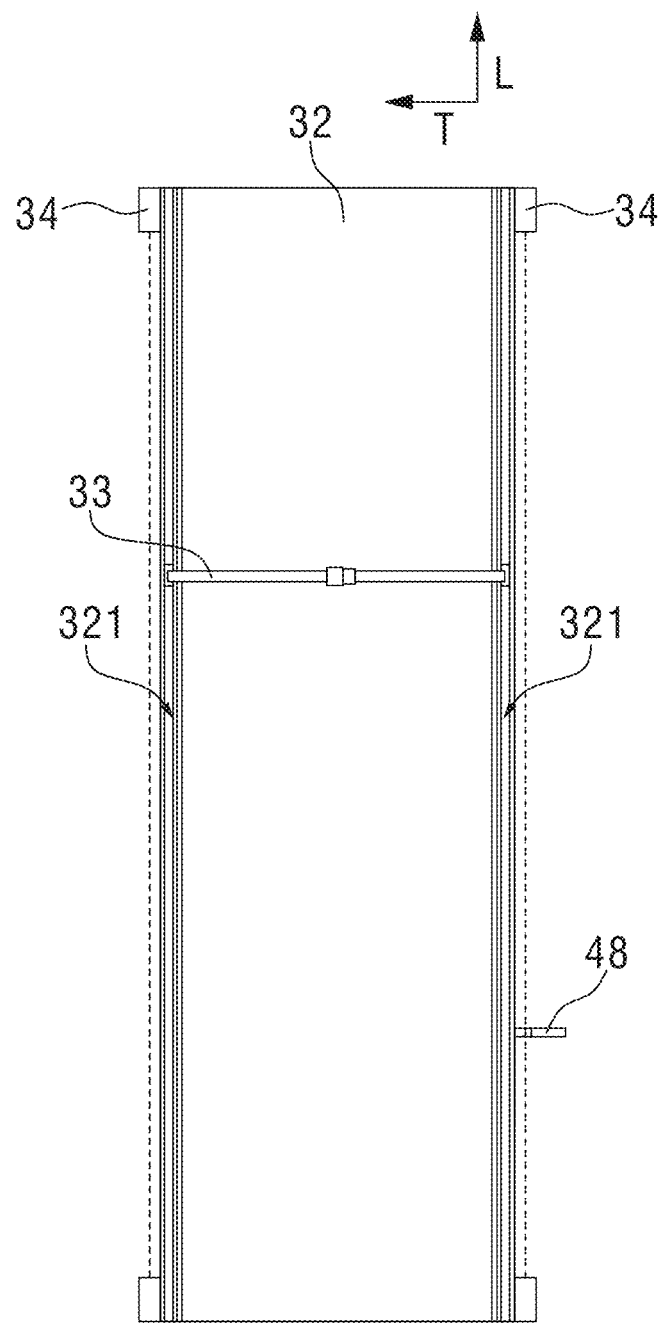
FIG. 5 is a top view of a partial structure of the bed according to an exemplary embodiment of the present disclosure.

FIG. 4 is a side view of a partial structure of the hospital bed in FIG. 1. FIG. 5 is a top view of a partial structure of the hospital bed in FIG. 1. As shown in FIG. 1, FIG. 4 and FIG. 5, in the exemplary embodiment, the auxiliary component 30 further comprises a restraint belt 33. The second bed board 32 has a runner 321 on each of its two ends along the adjustment direction T. The runners 321 extend along the length direction L of the second bed board 32. The two ends of the restraint belt 33 may be respectively slidably set in the runners 321. In this way, it is easy to fix an object to be scanned carried on the second bed board 32, and it prevents one part of the object to be scanned from being placed on the two sides of the second bed board 32 along the adjustment direction T, thereby preventing the object to be scanned from being squeezed by the second bed board 32 and the wall of the access hole when the second bed board 32 moves in the adjustment direction T.

As shown in FIG. 1, FIG. 2, FIG. 4 and FIG. 5, in the exemplary embodiment, the auxiliary component 30 further comprises two laser intrusion detectors 34 and a control mechanism 37. The detection regions of the two laser intrusion detectors 34 may be respectively arranged on the two sides of the second bed board 32 along the adjustment direction T. The dashed lines in FIG. 5 represent the laser paths of the two laser intrusion detectors 34. The control mechanism (controller) 37 may be configured to control the action of the first moving and supporting mechanism 40 or sending an alarm based on an output signal of the laser intrusion detectors 34. For example, when the laser intrusion detectors 34 detect that an object has entered a detection region, the control mechanism 37 may control the drive member 48 configured as a drive motor to stop the movement or sends an audible and visual alarm to alert the user. This helps to prevent the object to be scanned from being squeezed by the second bed board 32 and the wall of the access hole when the second bed board 32 moves in the adjustment direction T. In an exemplary embodiment, the control mechanism (controller) 37 may include processing circuitry that is configured to perform one or more operations/functions of the control mechanism (controller) 37. The control mechanism (controller) 37 may include a memory and/or be configured to access an external memory.

As shown in FIG. 1, in the exemplary embodiment, the auxiliary component 30 may further comprise two pressure sensors 35 (only one of which is shown in FIG. 1). The two pressure sensors 35 may be connected to the second bed board 32 and respectively arranged on the two sides of the second bed board 32 along the adjustment direction T. The pressure sensors 35 may be, for example, film pressure sensors. The control mechanism 37 may be configured to control the action of the first moving and supporting mechanism 40 or sending an alarm based on an output signal of the pressure sensors 35. For example, when a pressure sensor 35 is triggered, the control mechanism 37 controls the drive member 48 configured as a drive motor to stop the movement or sends an audible and visual alarm to alert the user. This helps to prevent the object to be scanned from being squeezed by the second bed board 32 and the wall of the access hole when the second bed board 32 moves in the adjustment direction T.

In other exemplary embodiments, one or more of a restraint belt, a laser intrusion detector, and a pressure sensor may be selectively provided.

Figure 6:
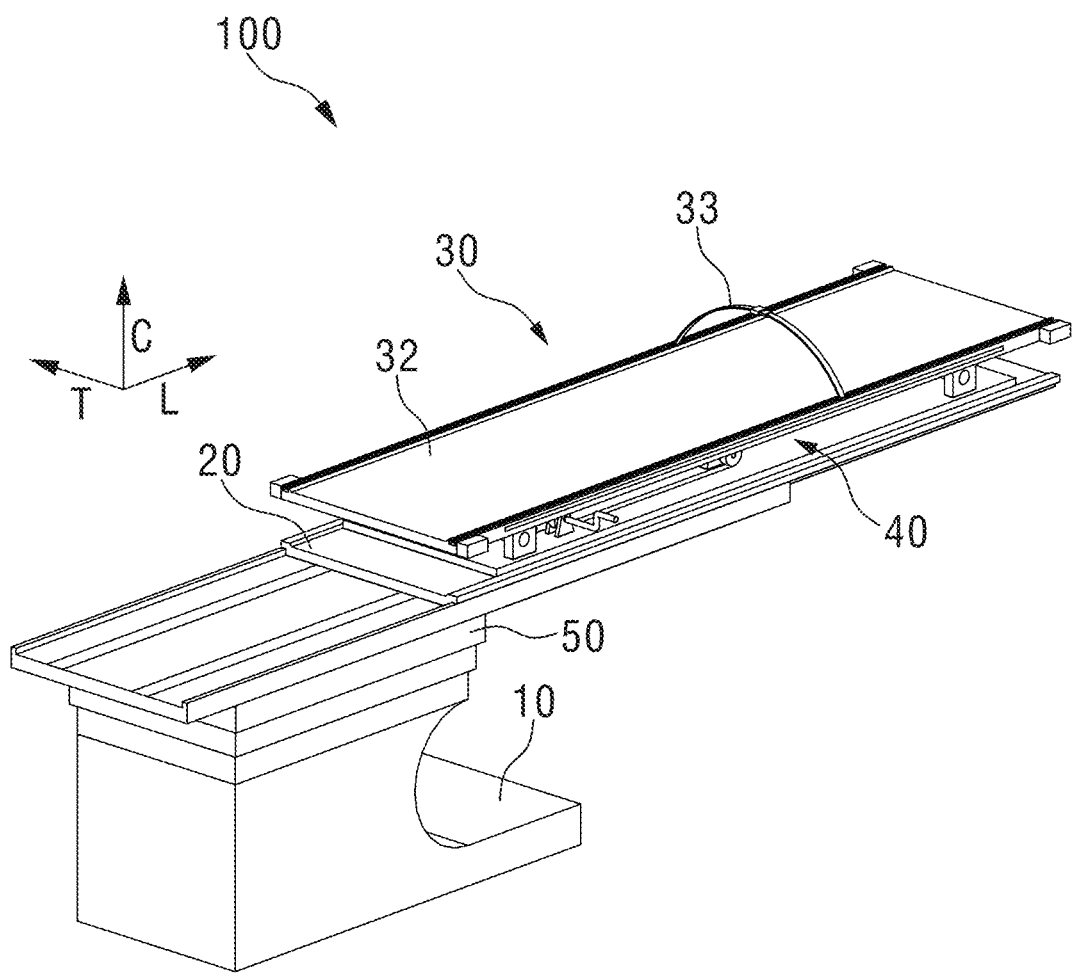
FIG. 6 is a patient bed according to an exemplary embodiment of the present disclosure.

In the exemplary embodiment, the second moving and supporting mechanism 50 may drive the first bed board 20 to move along the bearing direction C through, for example, an air cylinder structure, and the second moving and supporting mechanism 50 may drive the first bed board 20 to move along the length direction of the first bed board 20 through, for example, a rack and pinion structure, but it is not limited thereto. FIG. 6 shows the status of the first bed board 20 after moving along the length direction of the first bed board 20.

Figure 7:
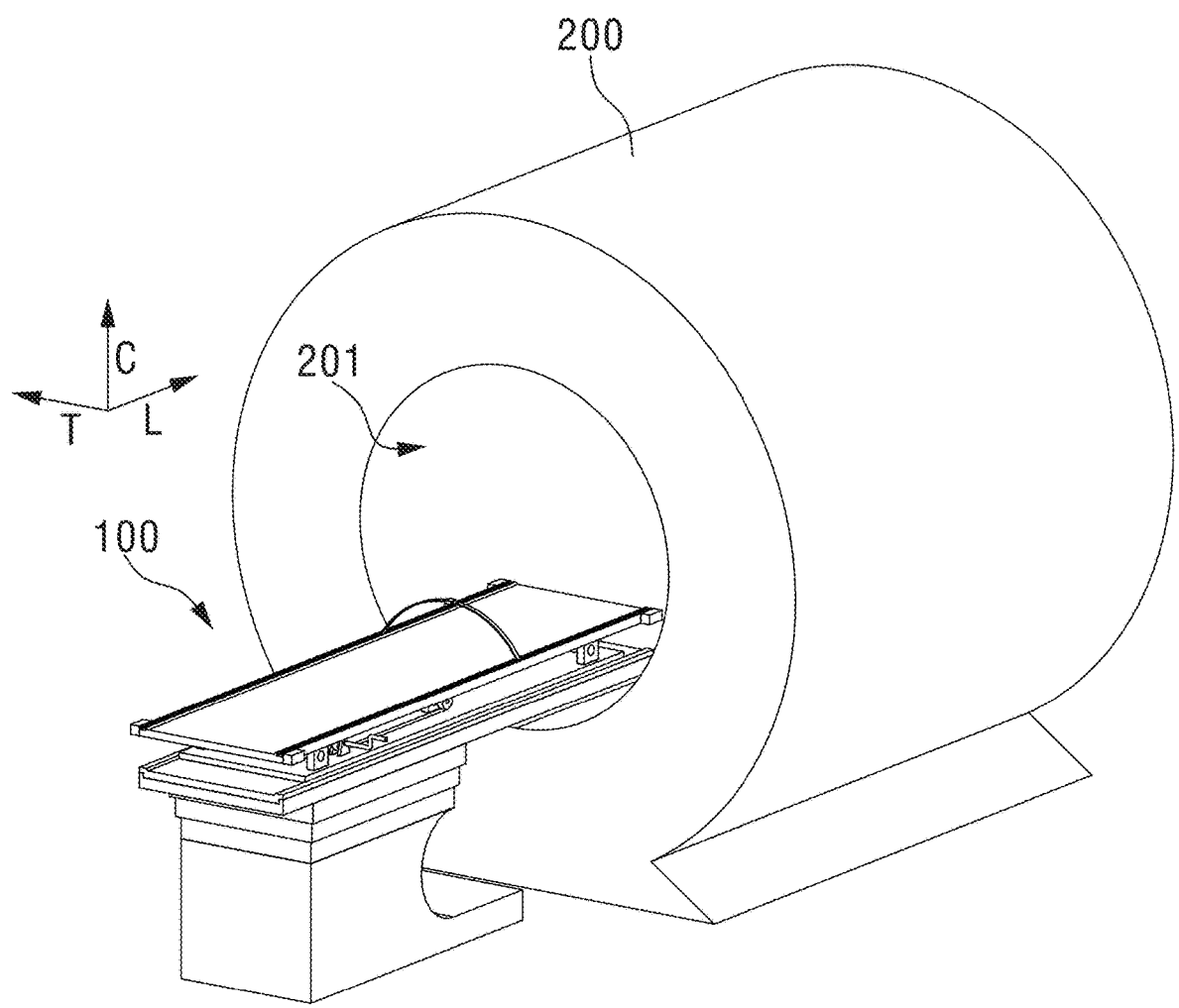
FIG. 7 is a magnetic resonance imaging system according to an exemplary embodiment of the present disclosure.

The present disclosure also provides a magnetic resonance imaging system. FIG. 7 is a schematic structural diagram of an exemplary embodiment of the magnetic resonance imaging system. As shown in FIG. 7, the magnetic resonance imaging system may comprise a magnetic field generating mechanism 200 and a hospital bed 100 shown in FIG. 1. The magnetic field generating mechanism 200 may include an access hole 201 extending in a linear direction. The magnetic field generating mechanism 200 can generate a main magnetic field and a gradient magnetic field required for magnetic resonance imaging in the access hole 201. Both the length direction of the first bed board 20 and the length direction L of the second bed board 32 may be parallel to the extension direction of the access hole 201. The first bed board 20 can extend into the access hole 201 along the extension direction of the access hole 201. The hospital bed of the magnetic resonance imaging system can be used for lateral movement of an object to be scanned carried on the second bed board along the adjustment direction.

It should be understood that, although this description is given to the various embodiments, not each embodiment contains only one independent technical solution. This way of description is only for clarity, and those skilled in the art should regard the description as a whole. The technical solutions in each embodiment can also be appropriately combined to form other implementations that can be understood by those skilled in the art.

The series of detailed descriptions above are only specific descriptions of some feasible embodiments of the present disclosure, which are not intended to limit the scope of the present disclosure. Any equivalent embodiments or changes, for example, combination, division or repetition of features, shall be covered within the scope of the present disclosure.

To enable those skilled in the art to better understand the solution of the present disclosure, the technical solution in the embodiments of the present disclosure is described clearly and completely below in conjunction with the drawings in the embodiments of the present disclosure. Obviously, the embodiments described are only some, not all, of the embodiments of the present disclosure. All other embodiments obtained by those skilled in the art on the basis of the embodiments in the present disclosure without any creative effort should fall within the scope of protection of the present disclosure.

It should be noted that the terms "first", "second", etc. in the description, claims and abovementioned drawings of the present disclosure are used to distinguish between similar objects, but not necessarily used to describe a specific order or sequence. It should be understood that data used in this way can be interchanged as appropriate so that the embodiments of the present disclosure described here can be implemented in an order other than those shown or described here. In addition, the terms "comprise" and "have" and any variants thereof are intended to cover non-exclusive inclusion. For example, a process, method, system, product or equipment comprising a series of steps or modules or units is not necessarily limited to those steps or modules or units which are clearly listed, but may comprise other steps or modules or units which are not clearly listed or are intrinsic to such processes, methods, products or equipment.

References in the specification to "one embodiment," "an embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

The exemplary embodiments described herein are provided for illustrative purposes, and are not limiting. Other exemplary embodiments are possible, and modifications may be made to the exemplary embodiments. Therefore, the specification is not meant to limit the disclosure. Rather, the scope of the disclosure is defined only in accordance with the following claims and their equivalents.

Embodiments may be implemented in hardware (e.g., circuits), firmware, software, or any combination thereof. Embodiments may also be implemented as instructions stored on a machine-readable medium, which may be read and executed by one or more processors. A machine-readable medium may include any mechanism for storing or transmitting information in a form readable by a machine (e.g., a computer). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact results from computing devices, processors, controllers, or other devices executing the firmware, software, routines, instructions, etc. Further, any of the implementation variations may be carried out by a general-purpose computer.

For the purposes of this discussion, the term "processing circuitry" shall be understood to be circuit(s) or processor(s), or a combination thereof. A circuit includes an analog circuit, a digital circuit, data processing circuit, other structural electronic hardware, or a combination thereof. A processor includes a microprocessor, a digital signal processor (DSP), central processor (CPU), application-specific instruction set processor (ASIP), graphics and/or image processor, multi-core processor, or other hardware processor. The processor may be "hard-coded" with instructions to perform corresponding function(s) according to aspects described herein. Alternatively, the processor may access an internal and/or external memory to retrieve instructions stored in the memory, which when executed by the processor, perform the corresponding function(s) associated with the processor, and/or one or more functions and/or operations related to the operation of a component having the processor included therein.

In one or more of the exemplary embodiments described herein, the memory is any well-known volatile and/or non-volatile memory, including, for example, read-only memory (ROM), random access memory (RAM), flash memory, a magnetic storage media, an optical disc, erasable programmable read only memory (EPROM), and programmable read only memory (PROM). The memory can be non-removable, removable, or a combination of both.

REFERENCE LIST

10 Bed frame
20 First bed board
21 Mounting and positioning groove
30 Auxiliary component
31 Connecting frame
311 Mounting and positioning portion
32 Second bed board
321 Runner
33 Restraint belt
34 Laser intrusion detector
35 Pressure sensor
37 Control mechanism (controller)
38 Connecting bolt
40 First moving and supporting mechanism
41 Screw
42 Moving block
43 Supporting assembly
431 Sliding rod
432 Slider
45 First transmission wheel
46 Second transmission wheel
47 Transmission belt
48 Drive member
50 Second moving and supporting mechanism
100 Hospital bed
200 Magnetic field generating mechanism
201 Access hole
C bearing direction
T Adjustment direction
L Length direction of the second bed board

The invention claimed is:
1. A hospital bed comprising:
a bed frame;
a first bed board connected to the bed frame and configured to carry an object along a bearing direction; and
an auxiliary component, comprising:
a connecting frame detachably connected to the first bed board;
a first moving and supporting mechanism connected to the connecting frame; and
a second bed board connected to the first moving and supporting mechanism and configured to carry an object along the bearing direction, the second bed board being arranged on one side of the first bed board along the bearing direction, wherein the first moving and supporting mechanism is configured to drive the second bed board to move relative to the first bed board along an adjustment direction, the adjustment direction being perpendicular to the bearing direction.

2. The hospital bed as claimed in claim 1, wherein the first moving and supporting mechanism comprises:
a screw rotatably connected to the connecting frame, wherein an axial direction of the screw is parallel to the adjustment direction;
a moving block fixedly connected to the second bed board and threadedly connected to the screw; and
a supporting assembly that includes:
a sliding rod fixedly connected to the connecting frame or the second bed board, and extends along the adjustment direction; and
a set of sliders fixedly connected to the connecting frame or the second bed board, whichever not fixedly connected to the sliding rod, the set of sliders being slidably sleeved on the sliding rod.

3. The hospital bed as claimed in claim 2, wherein the first moving and supporting mechanism includes two of the supporting assemblies arranged along a length direction of the second bed board, the screw and the moving block being arranged between the two supporting assemblies along the length direction of the second bed board, wherein the length direction of the second bed board is perpendicular to the bearing direction and the adjustment direction.

4. The hospital bed as claimed in claim 3, wherein the first moving and supporting mechanism further comprises:
a first transmission wheel fixedly connected to one end of the screw coaxially;
a second transmission wheel rotatably connected to the connecting frame, the second transmission wheel and the first transmission wheel being arranged along the length direction of the second bed board;
a transmission belt wound on the first transmission wheel and the second transmission wheel; and
a drive member connected to the second transmission wheel and configured to drive the second transmission wheel to rotate, wherein the drive member is a handle or a drive motor.

5. The hospital bed as claimed in claim 1, wherein the auxiliary component further comprises a restraint belt, the second bed board including a runner on each of its two ends along the adjustment direction, wherein the runner extends along the length direction of the second bed board, the length direction of the second bed board is perpendicular to the adjustment direction and the bearing direction, and the two ends of the restraint belt are respectively slidably set in the runners.

6. The hospital bed as claimed in claim 1, wherein the auxiliary component further comprises:
two laser intrusion detectors, the detection regions of which are respectively arranged on the two sides of the second bed board along the adjustment direction; and
a control mechanism configured to control the first moving and supporting mechanism or send an alarm based on an output signal of the laser intrusion detectors.

7. The hospital bed as claimed in claim 1, wherein the auxiliary component further comprises:
a plurality of pressure sensors connected to the second bed board and arranged on the two sides of the second bed board along the adjustment direction, and
a control mechanism configured to control the first moving and supporting mechanism or send an alarm based on an output signal of the pressure sensors.

8. The hospital bed as claimed in claim 1, wherein:
the connecting frame and the first moving and supporting mechanism are arranged on the side of the second bed board facing the first bed board along the bearing direction,
the first bed board has a plurality of mounting and positioning grooves provided along a direction opposite to the bearing direction,
the connecting frame has a plurality of mounting and positioning portions, each of the mounting and positioning portions being inserted into one of the mounting and positioning grooves along a direction opposite to the bearing direction to limit a relative displacement of the first bed board and the connecting frame along a direction perpendicular to the bearing direction, and
the auxiliary component further comprises a plurality of connecting bolts, each of the connecting bolts penetrating one of the mounting and positioning portions in a direction opposite to the bearing direction passing through the groove wall of one of the mounting and positioning grooves, and being threadedly connected to the first bed board.

9. The hospital bed as claimed in claim 1, wherein:
the hospital bed further comprises a second moving and supporting mechanism,
the second moving and supporting mechanism is connected to the bed frame and the first bed board,
the second moving and supporting mechanism is configured to drive the first bed board to move along the length direction of the first bed board and the bearing direction,
the length direction of the first bed board, the bearing direction, and the adjustment direction are perpendicular to each other, and
the length direction of the first bed board is parallel to the length direction of the second bed board.

10. A magnetic resonance (MR) imaging system comprising:
a MR scanner including an access hole extending in a linear direction, the MR scanner being configured to generate a main magnetic field and a gradient magnetic field adapted for magnetic resonance imaging in the access hole, and
a hospital bed including:
a bed frame;
a first bed board connected to the bed frame and configured to carry an object along a bearing direction; and
an auxiliary component, comprising:
a connecting frame detachably connected to the first bed board;
a first moving and supporting mechanism connected to the connecting frame; and
a second bed board connected to the first moving and supporting mechanism and configured to carry an object along the bearing direction, the second bed board being arranged on one side of the first bed board along the bearing direction, wherein the first moving and supporting mechanism is configured to drive the second bed board to move relative to the first bed board along an adjustment direction, the adjustment direction being perpendicular to the bearing direction.

11. The MR imaging system as claimed in claim 10, wherein:
both the length direction of the first bed board and the length direction of the second bed board are parallel to the linear direction of the access hole,
the adjustment direction is perpendicular to the length direction of the first bed board and the bearing direction, and
the first bed board can extend into the access hole along the extension direction of the access hole.

* * * * *